United States Patent [19]

Hoenig

[11] Patent Number: 4,996,479
[45] Date of Patent: Feb. 26, 1991

[54] MAGNETOMETER DEVICE WITH A DEWAR VESSEL FOR MEASURING WEAK MAGNETIC FIELDS

[75] Inventor: Eckhardt Hoenig, Erlangen, Fed. Rep. of Germany

[73] Assignee: Siemens Aktiengesellschaft, Berlin & Munich, Fed. Rep. of Germany

[21] Appl. No.: 408,108

[22] Filed: Sep. 15, 1989

[30] Foreign Application Priority Data

Sep. 16, 1988 [DE] Fed. Rep. of Germany ....... 3831545

[51] Int. Cl.$^5$ .................. G01R 33/035; A61B 5/05; F17C 13/02
[52] U.S. Cl. .................................. 324/248; 128/653; 62/49.1; 220/901
[58] Field of Search .............. 324/248; 128/653; 220/3, 901; 505/846; 62/45.1, 48.1, 49.1

[56] References Cited

U.S. PATENT DOCUMENTS

| | | | |
|---|---|---|---|
| 4,689,559 | 8/1987 | Hastings et al. | 324/248 |
| 4,700,135 | 10/1987 | Hoenig | 324/248 |
| 4,749,946 | 6/1988 | Hoenig | 324/248 |
| 4,793,355 | 12/1988 | Crum et al. | 324/248 X |
| 4,827,217 | 5/1989 | Paulson | 324/248 |

FOREIGN PATENT DOCUMENTS

| | | |
|---|---|---|
| 0156240 | 2/1985 | European Pat. Off. . |
| 0200958 | 12/1986 | European Pat. Off. . |
| 3247543 | 6/1984 | Fed. Rep. of Germany . |
| 0071972 | 4/1985 | Japan ........................... 324/248 |
| 85/04489 | 10/1985 | World Int. Prop. O. . |

OTHER PUBLICATIONS

Patent Abstracts of Japan, vol. 10, No. 285; Sep. 27, 1986; JP 61-104681, 5/22/86.
Physics Today, Mar. 1986, pp. 36–44; "Squids, Brains and Gravity Waves".
J. Phys. E.: Sci. Instrum., vol. 13 (1980), pp. 801–813.
IEEE Transactions on Electron Devices, vol. ED-27, No. 10 (1980), 1896–1908.
Book "Biomagnetism—Berlin 1980" (1981), pp. 3–31.

*Primary Examiner*—Gerard R. Strecker
*Attorney, Agent, or Firm*—Kenyon & Kenyon

[57] ABSTRACT

A magnetometer device for measuring the magnetic fields caused by field sources includes a Dewar vessel that has an interior with access through a neck. The interior contains several superconducting gradiometers as well as corresponding SQUIDs. The Dewar vessel is arranged underneath or laterally to the field source. An insertion vessel for a liquid refrigerant which is thermally coupled to the SQUIDs and is located in the interior. The gaseous refrigerant taken from the insertion vessel is supplied to the gradiometers through hose lines. The refrigerant escaping into the interior is discharged to the outside via the neck. A throttling device is inserted into the neck to prevent warmer gaseous refrigerant from entering the interior.

19 Claims, 3 Drawing Sheets

MAGNETOMETER DEVICE WITH A DEWAR VESSEL FOR MEASURING WEAK MAGNETIC FIELDS

BACKGROUND OF THE INVENTION

The present invention relates to a magnetometer device for measuring weak magnetic fields.

A known magnetometer device for measuring weak magnetic fields from at least one field source comprises a Dewar vessel that defines an inner region. Access to the inner region is through a neck. The inner region contains several superconducting gradiometers as well as their associated SQUIDs. The gradiometers and SQUIDs are cooled by a refrigerant that is fed through the neck from outside the Dewar vessel. This type of magnetometer device is suggested in the publication "Physics Today" of March 1986 from pages 36–44.

Very weak magnetic fields can be measured with superconducting quantum interferometers, sometimes referred to by the acronym "SQUID" which stands for Superconducting Quantum Interference Device. Examples of SQUIDs can be found in, for example, "*J. Phys. E.: Sci. Instrum.*", Vol. 13, 1980, pages 801-813, or "IEEE Trans. Electron Dev.", Vol. ED-27, No. 10, October 1980, pages 1896-1908. One preferred application for these interferometers is in the area of medical diagnostics. For example, magnetocardiography and magnetoencephalography involve measuring the magnetic fields of heart and brain waves. These waves have magnetic field strengths with magnitudes near 50 pT and 0.1 pT, respectively. See, for example "Biomagnetism-Proceedings Third International Workshop On Biomagnetism, Berlin, 1980", Berlin, N.Y. 1981, pages 3-31. It should be possible to detect these very weak fields in the presence of relatively large interference fields.

Devices are known for measuring such biomagnetic fields. See for example, German Patent No. 3,247,543, corresponding to U.S. Pat. No. 4,749,946. These devices can be designed with one or more channels. The devices contain SQUID magnetometers with gradiometers of the first or higher order, depending on the number of channels as discussed in the "Physics Today" article reference above.

The superconducting gradiometers and their associated SQUIDs are arranged within a Dewar vessel. When cooling the superconducting components, particularly the highly sensitive SQUIDS, it is necessary to avoid direct and indirect magnetic interference. Cooling techniques that use refrigerators have not been favored. Refrigerators generate magnetic fields that cause interference and have moving parts that cause vibrations. These magnetic fields preclude the use of refrigerators. Cooling is thus done by supplying refrigerant such as liquid helium. The refrigerant must be replenished at regular time intervals of several days.

The Dewar vessels containing the superconducting gradiometers and SQUIDs in known magnetometers are arranged above the detectable field sources of the patient to be examined. A Dewar vessel for a multichannel magnetometer device typically contains 15 to 30 liters of liquid refrigerant that ends up suspended directly above the patient. All this refrigerant poses potential danger for the patient located directly underneath. It is possible that a considerable quantity of cold gas would pour over the patient in response to a sudden breakdown of the insulating vacuum or if a sudden damage to a Dewar vessel trips the safety valves. For example, 15 to 30 liters of liquid helium would generate about 10 to 30 cubic meters of cold helium gas in such an emergency. This cold gas is difficult to keep away from the patient, especially if the examination is carried out in a shielded enclosure. An overhead arrangement of Dewar vessels can also be perceived as disagreeable by the patient. Thus there is a need to provide a magnetometer device of this type in which the Dewar vessel is arranged without potential danger to the patient while still not using refrigerators that cause magnetic interference.

SUMMARY OF THE INVENTION

This need is fulfilled by the magnetometer device of the present invention where the Dewar vessel is arranged below or lateral relative to at least one field source, e.g., the patient. A special insertion vessel is provided in the interior of the Dewar vessel into which liquid refrigerant can be fed via a pipeline leading through the neck. SQUIDs are located in or at the insertion vessel. Gaseous refrigerant taken from the insertion vessel is fed to the superconducting gradiometers via one or more tubular connecting lines. The gaseous refrigerant escaping into the interior at the gradiometers is discharged to the outside through the neck. A throttling or choking device is inserted into the neck to inhibit normal gaseous refrigerant from flowing back into the interior.

The advantages connected with this embodiment of the invention are that an overhead arrangement of the Dewar vessel is avoided and effective cooling of the superconducting parts of the device is ensured. Undesired convection of exhaust gas of the refrigerant is also prevented. Tubular connecting lines provide an undisturbed supply of cold exhaust gas to the superconducting gradiometers even though they are arranged higher than the insertion vessel. The refrigerant normally attempts to flow in one direction due to temperature and density differences. A throttling or choke device is arranged in the vicinity of the neck to prevent warmer exhaust gas from flowing back from the outside into the interior.

DETAILED DESCRIPTION

Figure 1:
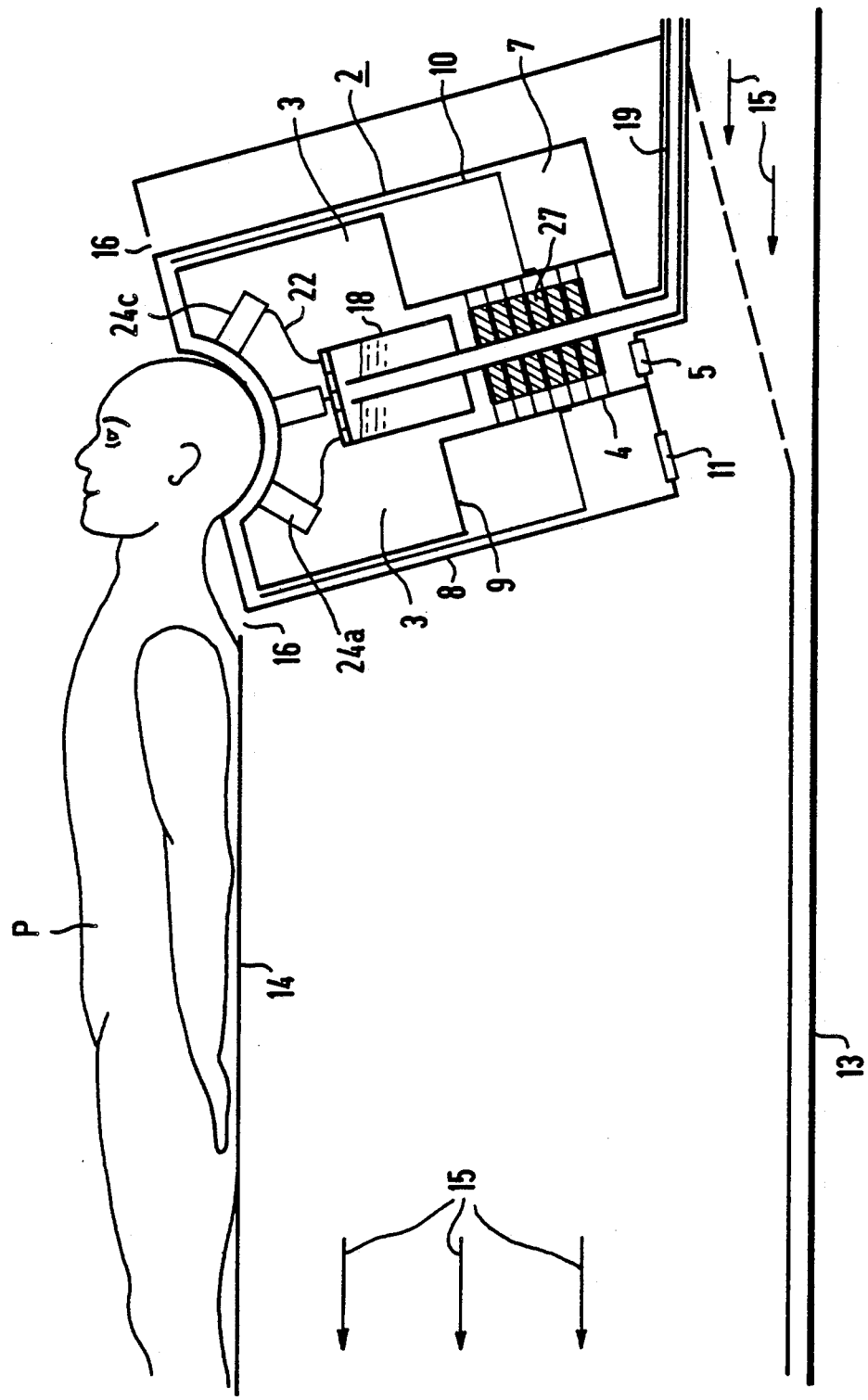
FIG. 1 shows a magnetometer device in a patient examining table that is constructed according to the present invention.

Known SQUID magnetometers for single or multichannel devices contain at least one superconducting gradiometer for the detection of the magnetic signals (magnetic fluxes or flux gradients) emanating from a field source, especially from the heart or the brain of a patient. The detected signals are then fed via superconducting or normal-conducting connecting leads to a number of SQUIDs corresponding to the number of channels. These SQUIDs can likewise be combined in an array and are connected to electronic circuitry. This structure, being known, is not shown in the drawings.

According to the longitudinal section shown in FIG. 1, a double walled Dewar vessel 2 containing the superconducting magnetometers is shown in a design having rotational symmetry. The interior 3 of this vessel permits access via a relatively narrow neck 4. At least one safety valve 5 is provided in the neck region 4 to allow the cold gas to escape to the outside in case of an accident. The space 7 between the walls 8 and 9 of the vessel 2 is evacuated in a known manner and may contain superinsulation which is not shown in the figure. In addition, a thermal radiation shield 10 may be arranged between the walls 8 and 9. For the vacuum space 7, at least one safety valve 1 is provided in the neck region.

The Dewar vessel 2 is rotationally symmetrical in design and arranged so that its neck 4 is lower than its interior 3. According to the illustrated embodiment, the neck 4 is inclined downward at an angle. This kind of arrangement makes it possible for the vessel 2 to be integrated into a patient examining table 14 standing on a floor 13. According to the shown embodiment, the Dewar vessel 2 is tilted so that the patient P is in a comfortable lying position. The patient P is depicted in a position for examination of the magnetic field of the brain. For this reason the shape of the Dewar vessel 2 is properly adapted to the shape of the head of the patient.

The full cross section of the understructure of the patient examining table 14 is advantageously utilized for both the passive and active low pressure venting of the Dewar vessel. The corresponding flow conditions of an active ventilation are indicated with arrows in the figure by lines 15. In addition, a suction gap 16 can be provided around the Dewar vessel 2 in the patient examining table 14. Opening the safety valves 5 or 11 from the interior 3 of the vacuum space 7 causes the corresponding cold gas to then escape into the understructure of the patient examining table 14 where it can be suctioned through the gap 16.

The arrangement of the Dewar vessel 2 below the patient P has the further advantage that a large mass can be arranged underneath the patient to limit vibration amplitudes. These vibrations can lead to inadvertent magnetic disturbances.

Figure 2:
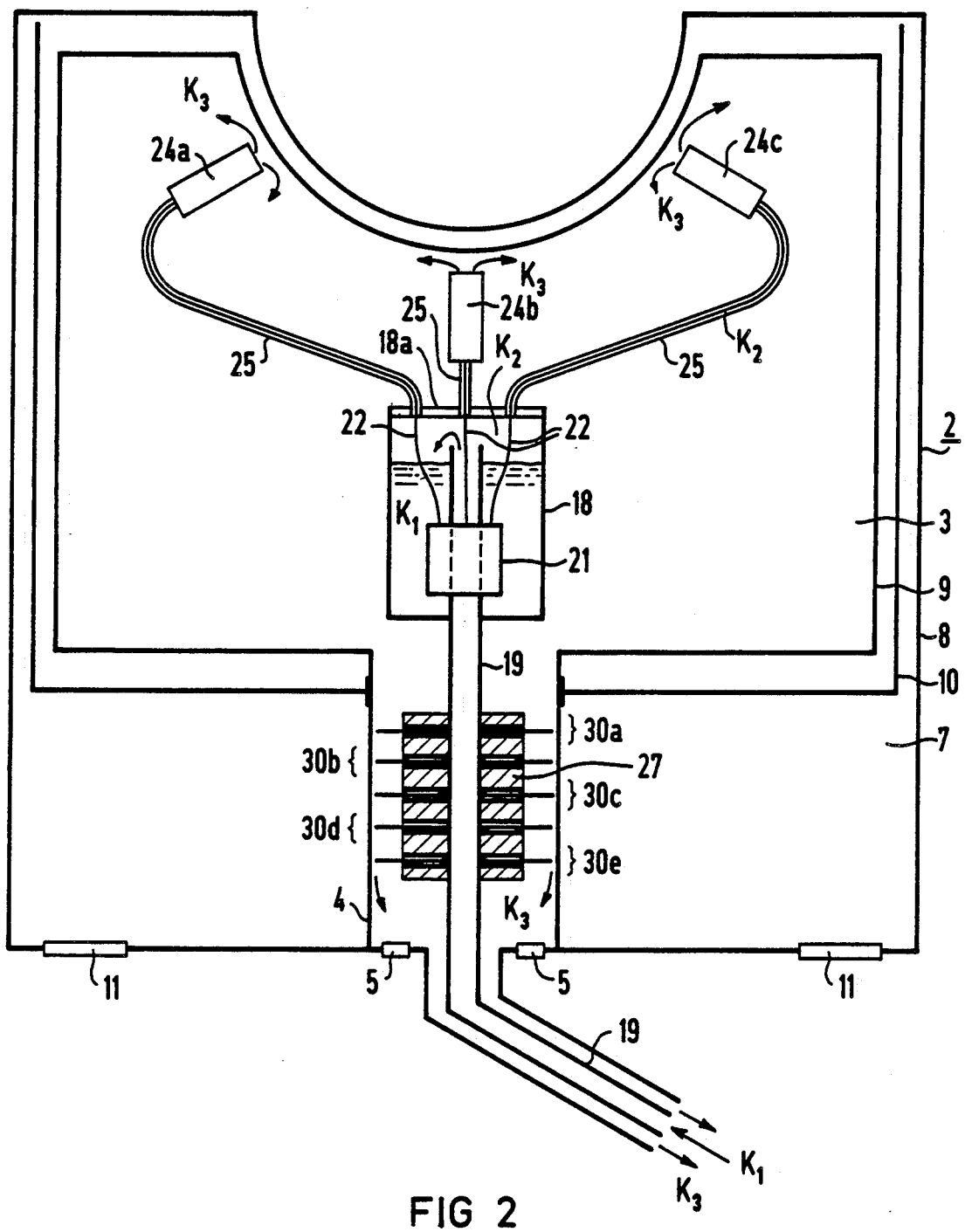
FIG. 2 shows a Dewer vessel for the magnetometer device according to the present invention.

FIG. 2 shows a detailed longitudinal cross section of the Dewar vessel 2. An insertion container 18 containing a quantity of a liquid refrigerant $K_1$ is placed into the interior 3. For example, two to three liters of liquid helium refrigerant are required for a given work day to cool the superconducting parts of the device either directly or indirectly. The refrigerant is replenished from below via a pipeline 19 which extends through the neck 4. The pipeline 19 is a vacuum-insulated connection which is cooled by the flow of the exhaust gas of the refrigerant. The exhaust gas flows to an external supply vessel, not shown. Replenishing of the liquid refrigerant can take place here daily.

Temperature sensitive parts, particularly the SQUIDs, are arranged in or near the insertion vessel 18. The SQUIDs, not shown in the figure, are combined in an array which is located on a chip 21. The SQUIDs are connected using, for example, superconducting leads 22 to corresponding gradiometers 24a–24c. Although only the three gradiometers 24a–24c are shown, the maximum number can be substantially higher. The electrically conducting leads 22 are arranged within the hose-like refrigerant lines 25 which may be made of plastic. The electrically conducting leads 22 can also be provided with integrated hoselike refrigerant lines. Foil-like conductors can be coated on one of the flat sides of the foil with a hose-like enclosure by, for example, cementing. These leads should be considered a part of the hose-like refrigerant line 25.

Relatively cold refrigerant $K_2$ generated in the insertion vessel 18 is fed to the gradiometers 24a–24c through lines 25. The insertion vessel 18 is provided with a lid 18a that is designed to act as a gas distributor. The refrigerant lines 25 are connected to the lid 18a. The exhaust gas rate can be adjusted as required by supplying a suitable amount of heat into the insertion vessel 18. For example, the heat can be conducted into the insertion vessel 18 from the outside by a heat-conducting rod made of fiber glass reinforced material. The cold gas then enters the interior 3 at the gradiometers where it then leaves the interior region through the neck 4. Special care is needed to prevent a reverse flow of warmer exhaust gas into the interior region 3 due to convection caused by temperature and density differences. This objective can be allowed using a throttling or choke device 27 in the neck 4 to leave a relatively narrow gap for the exhaust gas $K_3$. The gap causes the exhaust gas $K_3$ to escape to the outside because it is under a larger high pressure in the interior. Because of this pressure differential resulting in the outward flow of the exhaust gas $K_3$, the warmer exhaust gas is prevented from flowing back into the interior region 3 of the vessel 2. This exhaust gas can also be utilized for cooling further parts of the device such as the radiation shield 10. The interior 3 can be filled with glass balls to further limit possible cold gas convection.

Figure 3:
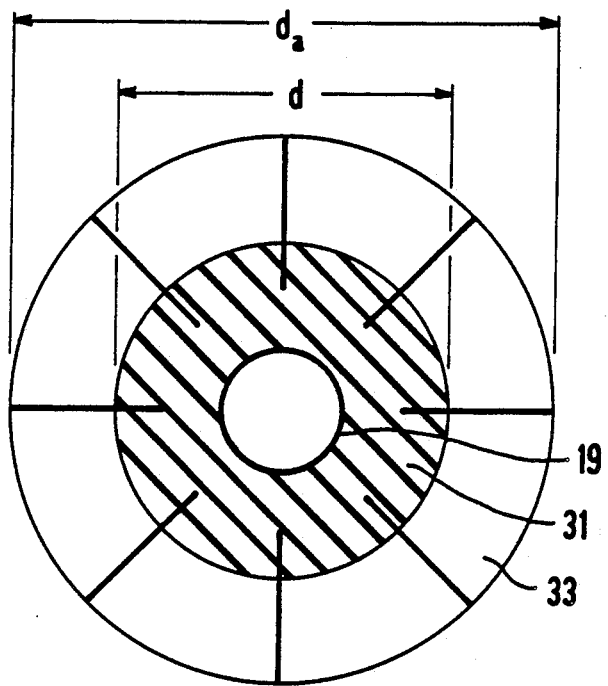
FIGS. 3 and 4 show different perspectives of a throttling device for the Dewar vessel of the present invention.
Figure 4:
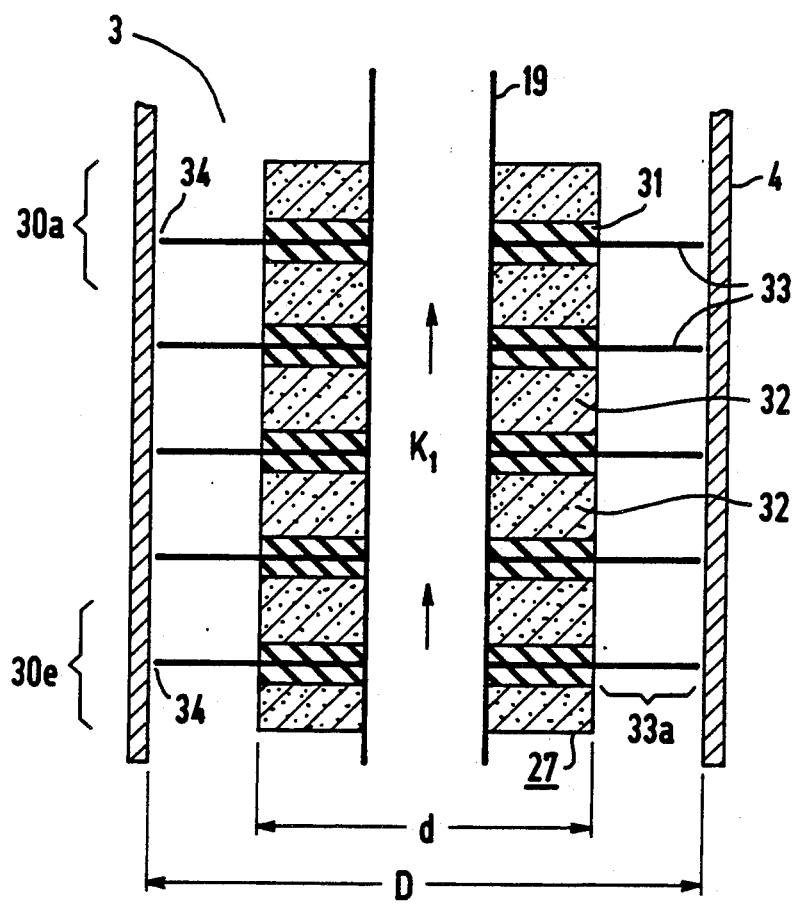

An embodiment of the choke device 27 is schematically shown in FIGS. 3 and 4 as a cross section and longitudinal section, respectively. It is designed as a circular cylinder enclosing the pipeline 19 for the liquid refrigerant $K_1$. The choke device 27 can, for example, be slipped onto the pipeline and contains a stack of circular cylindrical elements 30a–30e. Each of these choke or throttling elements has a central washer-like holding clamp 31 which can be made of fiber glass reinforced plastic. The outside diameter d of each holder 31 is distinctly smaller than the inside diameter D of the tubular neck of the Dewar vessel. On the opposite flat side of the individual holders there are circular cylindrical plugs 32 with a corresponding diameter d. These plugs, which can be made of a hard foam, serve to space the individual holders 31 from each other. Each holder 31 supports a washer-shaped plastic plate 33, which can be made of a special polyester foil. These relatively thin plates 33 have an outside diameter $d_a$ which is only slightly smaller than the inside diameter D of the neck 4. Thus, a small gap 34 remains between the inside wall of the neck 4 and the washer-shaped plastic plates 33 through which the exhaust gas $K_3$ escapes from the interior 3 of the Dewar vessel to the outside. The washer-shaped outer rim part 33a, extends laterally beyond the outer rim of the holder 31 of each thin plate 33 and is relatively flexible so that it can bend in case of accidental high pressure in the interior 3. This flexibility leads to a correspondingly larger cross section flow in the gaps 34 for the exhaust gas $K_3$. It is possible for the elastic outer rim parts 33a of the plates 33 to extend up to the inner wall of the neck 4. It is also possible for the gaps to be caused by deformation of the part 33a caused by high pressure exhaust gas $K_3$.

According to the embodiment shown in the figures, it is assumed that the Dewar vessel 2 has a wider extension of its interior 3 as compared to the neck region such as shown in European patent No. A0,200,958, incorporated herein by reference. In this case holding elements can be used which spread out after being introduced into the interior, or, a plug-in connection can be used which had been built in before, between the insertion vessel 18 and the gradiometers 24a–24c.

Dewar vessels that do not have enlarged extensions can be provided which pose no special problem for incorporating the present invention. In both forms of the vessel, however, the following two cases must be distinguished. (1) The SQUIDs can be integrated with the associated gradiometers to form modules so that only normal-conducting connections and the connection for the exhaust gas cooling need to be made. (2) The SQUIDs can be combined inside or near the insertion vessel so that superconducting connections to the gradiometers as well as the exhaust gas coolings of the gradiometers must be made.

In both cases, the lid 18a of the insertion vessel 18 acts as a gas distributor and is built in together with the gradiometers before the insertion vessel is put in place. In the first case, a metallic multiple plug can be advantageously provided (See EP-A-0, 200,958 mentioned above). Alternately, a flatter multiple coupling transformer can be used in the second case where the coupling takes place automatically when the insertion vessel is inserted.

It is not absolutely necessary for the magnetometer device that the insertion vessel 18 and the Dewar vessel 2 surrounding it have the same cylindrical axis. A freely movable standard position of the Dewar axis is obtained. If the insertion vessel is inclined relative to the Dewar axis by a predetermined angle. A horizontal Dewar axis provides convenient access to its crest region if the patient rests normally on an examining table. However, the insertion vessel must always be arranged so that only the gaseous refrigerant $K_2$ gets to its lid that is located above the refrigerant $K_1$. The neck 4 can be inclined downward, at an angle, to be horizontal in the case of a rotationally symmetrical design. In principle, the inclination of the neck is not particularly important. For reasons of simple assembly and mounting, a rotationally symmetric design with a neck pointing downward at an angle is advantageous.

What is claimed is:

1. A magnetometer device for measuring weak magnetic fields, of at least one field source comprising:
    a Dewar vessel arranged below or laterally to the at least one field source and having an interior region and a neck, said interior region being accessed via said neck;
    an insertion vessel disposed in the interior region of the Dewar vessel in which liquid refrigerant can be retained;
    a plurality of superconducting gradiometers and associated SQUIDs arranged in the interior region of the Dewar vessel, the SQUIDs being positioned in or at the insertion vessel;
    a pipeline terminating in said insertion vessel and extending through the neck feeding liquid refrigerant through the neck from outside the Dewar vessel;
    at least one hose line extending from the insertion vessel to the superconducting gradiometers feeding gaseous refrigerant to said gradiometers; and
    a throttling device positioned in the neck for inhibiting warmer gaseous refrigerant from flowing back into the interior region, said pipeline extending through said throttling device.

2. An apparatus as claimed in claim 1, wherein the throttling device comprises a stack of several washer-like throttling elements inserted in the neck to increase the flow resistance for the gaseous refrigerant and which, together with the inner wall of the neck, form at least one narrow gap for the gaseous refrigerant.

3. An apparatus as claimed in claim 2, wherein the throttling elements are elastic in at least a portion of their outer rim, the gap being formed or enlarged by bending of the outer rim in response to pressure caused by the gaseous refrigerant.

4. An apparatus as claimed in claim 2, wherein each throttling element includes:
    a central clamping holder that surrounds the pipeline for the refrigerant in the area of the neck;
    a washer-shaped plastic plate fastened to the central clamping holder.

5. An apparatus as claimed in claim 4, wherein the plastic plate has an outside diameter that is substantially larger than the outside diameter of the central clamping holder.

6. An apparatus as claimed in claim 4, wherein the plastic plate is made from a polyester foil.

7. An apparatus as claimed in claim 3, wherein each throttling element includes:
    a central clamping holder that surrounds the pipeline for the refrigerant in the area of the neck;
    a washer-shaped plastic plate fastened to the central clamping holder.

8. An apparatus as claimed in claim 6, wherein the plastic plate has an outside diameter that is substantially larger than the outside diameter of the central clamping holder.

9. An apparatus as claimed in claim 1, further comprising a lid on the insertion vessel, the hose line by attaching to an opening in the lid whereby the lid will function as a gas distributor for the hose line.

10. An apparatus as claimed in claim 1, further comprising electrical connecting leads between the SQUIDs and the gradiometers that are thermally coupled to the gaseous refrigerant flowing in the hose lines.

11. An apparatus as claimed in claim 10, wherein the connecting leads comprise at least part of the hose lines for carrying the gaseous refrigerant.

12. An apparatus as claimed in claim 1, further comprising glass balls that fill the interior region of the Dewar vessel.

13. An apparatus as claimed in claim 1, wherein the Dewar vessel is integrated in an examination table for a patient so that the field source above or lateral relative to the Dewar vessel.

14. An apparatus as claimed in claim 1, wherein the neck of the Dewar vessel lies below the interior region.

15. An apparatus as claimed in claim 13, wherein the examination table includes means for venting of the interior region of the Dewar vessel.

16. An apparatus as claimed in claim 15, wherein the venting means comprises passive underpressure venting means.

17. An apparatus as claimed in claim 15, wherein the venting means comprises active underpressure venting means.

18. An apparatus as claimed in claim 1, wherein the Dewar vessel has an axis that forms a predetermined angle relative to the insertion vessel in the interior region.

19. An apparatus as claimed in claim 1, wherein the Dewar vessel has rotational symmetry.

* * * * *